(12) United States Patent
Tagliaferri et al.

(10) Patent No.: US 10,926,100 B2
(45) Date of Patent: Feb. 23, 2021

(54) LASER DEVICE FOR SELECTIVE TREATMENT OF ACNE WITH REDUCED SKIN TEMPERATURE INCREASE

(71) Applicant: QUANTA SYSTEM S.P.A., Samarate (IT)

(72) Inventors: Marco Tagliaferri, Taino (IT); Fabio Cannone, Melzo (IT); Gianluca Grolla, Cassano Magnago (IT)

(73) Assignee: QUANTA SYSTEM S.P.A., Samarate (IT)

( * ) Notice: Subject to any disclaimer, the term of this patent is extended or adjusted under 35 U.S.C. 154(b) by 244 days.

(21) Appl. No.: 16/064,284

(22) PCT Filed: Dec. 19, 2016

(86) PCT No.: PCT/IB2016/057767
§ 371 (c)(1),
(2) Date: Jun. 20, 2018

(87) PCT Pub. No.: WO2017/109667
PCT Pub. Date: Jun. 29, 2017

(65) Prior Publication Data
US 2018/0369605 A1 Dec. 27, 2018

(30) Foreign Application Priority Data

Dec. 22, 2015 (IT) .................. 102015000086201

(51) Int. Cl.
*A61N 5/06* (2006.01)
*A61B 18/20* (2006.01)
(Continued)

(52) U.S. Cl.
CPC .......... *A61N 5/0616* (2013.01); *A61B 18/203* (2013.01); *A61B 2018/2035* (2013.01);
(Continued)

(58) Field of Classification Search
None
See application file for complete search history.

(56) References Cited

U.S. PATENT DOCUMENTS

| 6,605,080 | B1 | 8/2003 | Altshuler et al. |
| 2008/0091179 | A1* | 4/2008 | Durkin ................. A61B 18/203 606/9 |

(Continued)

FOREIGN PATENT DOCUMENTS

| RU | 2019192 C1 | 9/1994 |
| WO | WO2008008971 A1 | 1/2008 |
| WO | WO2011084863 A2 | 7/2011 |

*Primary Examiner* — Ankit D Tejani
(74) *Attorney, Agent, or Firm* — King & Schickli, PLLC

(57) ABSTRACT

A laser device for the selective treatment of acne comprising: a laser source (1) terminating in an optical collimator (2), which supplies a laser beam; said laser source (1) comprises a switch (13) which allows impulses of said laser beam with pre-defined duration to be transmitted; an opto-mechanical interface (3) comprising a lens (4) focusing the laser beam received from the optical collimator (2); an optical fibre (5) connected to said opto-mechanical interface (3); characterized in that said optical fibre (5) has a length greater than 15 m; and said device comprises a handpiece (10) connected to said optical fibre (5) where said handpiece (10) comprises an optical zoom system (11) which allows the diameter of the laser beam emerging from said handpiece (10) to be varied from 0.5 mm to 5 mm.

8 Claims, 5 Drawing Sheets

(51) Int. Cl.
  *A61B 18/22* (2006.01)
  *A61N 5/00* (2006.01)
  *A61N 5/067* (2006.01)

(52) U.S. Cl.
  CPC ............. *A61B 2018/2244* (2013.01); *A61B 2018/2266* (2013.01); *A61N 2005/007* (2013.01); *A61N 2005/063* (2013.01); *A61N 2005/067* (2013.01); *A61N 2005/0644* (2013.01); *A61N 2005/0659* (2013.01)

(56) References Cited

U.S. PATENT DOCUMENTS

| | | | | |
|---|---|---|---|---|
| 2008/0147054 A1* | 6/2008 | Altshuler | ............. | A61B 18/203 606/9 |
| 2013/0064515 A1* | 3/2013 | Shurgalin | ............. | G02B 6/3624 385/125 |
| 2013/0253411 A1* | 9/2013 | Rubinchik | .......... | A61F 9/00821 604/20 |
| 2014/0264097 A1* | 9/2014 | Heanue | .............. | G01N 15/1434 250/576 |
| 2014/0364924 A1* | 12/2014 | Dunleavy | ............. | G06Q 20/22 607/88 |
| 2015/0250542 A1 | 9/2015 | Islam | | |

* cited by examiner

LASER DEVICE FOR SELECTIVE TREATMENT OF ACNE WITH REDUCED SKIN TEMPERATURE INCREASE

TECHNICAL FIELD

The present invention refers to a laser device for the selective treatment of acne with reduced skin temperature increase.

BACKGROUND

A compact handheld portable device for treating a sebaceous follicle disorder in a dermal region of the skin is described in the document WO2008/008971.

The object of the present invention is to provide an extremely efficient laser device for the selective treatment of acne.

A further object is to provide a laser device for the selective treatment of acne with reduced skin temperature increase, which avoids damage to the surrounding tissues.

A further object is to provide a laser device for the selective treatment of acne with reduced skin temperature increase, able to reduce the heating effects of the portion of skin involved in the treatment.

According to the present invention, said objects and others are achieved by a laser device for the selective treatment of acne and by a method according to the attached claims.

Further characteristics of the invention are described in the dependent claims.

SUMMARY

According to the present invention a solution is provided for the selective treatment of acne guaranteeing optimization of the physical parameters that determine the temperature increase, $\Delta T$, which induces thermal damage of the sebaceous gland, simultaneously allowing dynamic control of some of them:
- wavelength $\lambda$, of 1726 nm, in general within the wavelength range 1690 nm-1750 nm, thus reducing the heating effects due to absorption of the water in the tissues surrounding the sebaceous gland, guaranteeing the minimum diffusion effect and therefore maximum value of the fraction f;
- P power>1 W thus guaranteeing an appropriate fluence for the process which is extremely stable in emission (fluctuations <3%) so as not to alter the process depth in the long term;
- laser beam having a flat top intensity distribution ($\eta \leq 15\%$) i.e. suitable for selective treatment of the sebaceous gland which does not induce damage in the surrounding tissues and with a diameter $\phi > 0.5$ mm more generally selectable from a range 0.5 mm-5.0 mm maintaining unchanged the laser beam intensity distribution and guaranteeing the possibility of penetrating the biological tissue in a selected manner;
- control of skin surface temperature, $Ti \in [-10° C.; +10° C.]$, without the use of any cryogen gas which can create thermal shocks to the human skin;
- duration of the laser impulse $\tau$ such as not to be longer than the time for diffusion of the heat by the sebaceous gland and such as to avoid heating of the tissue surrounding said gland.

The system subject of the present invention allows an optimal temperature distribution to be obtained within the biological tissue in order to achieve, with minimum laser radiation energy, the selective treatment of acne, reducing the interaction effect of the laser radiation with said tissue.

It should be added that the solution proposed, in addition to overcoming the limits of the acne treatment process, allows a "flat top" beam to be obtained, the intensity distribution of which is independent of the laser radiation release conditions and of the power of said laser radiation.

BRIEF DESCRIPTION OF THE DRAWING FIGURES

The characteristics and advantages of the present invention will be evident from the following detailed description of a practical embodiment thereof, illustrated by way of non-limiting example in the accompanying drawings, in which:

FIG. 1 shows the temperature increase $\Delta T$ induced by a laser beam at 1726 nm, having a uniform intensity distribution (flat top) on the right and a Gaussian distribution on the left, in the biological tissue with a fluence of 50 J/cm2 and beam diameter of 3.5 mm at the top and 1.5 mm at the bottom, where the simulation considers the sebaceous gland positioned on the Y axis with R=0 cm and at a skin surface depth of 0.6 mm, with the X axis showing the depth in cm and the Y axis the beam dimension in cm;

FIG. 2 shows the temperature increase profile $\Delta T$ along the vertical axis of the sebaceous gland R=0 induced by a laser beam with fluence equal to 50 J/cm2, having a Gaussian intensity profile with variation in the diameter of the optical laser beam from the lower curve to the upper curve equal to 0.25, 0.5, 1, 2, 3, 3.5, 4, 5 mm, where the dermis is found between segments A and D and the sebaceous gland is found between segments B and C;

FIG. 3 shows the temperature increase profile $\Delta T$ along the vertical axis of the sebaceous gland R=0 induced by a laser beam with fluence equal to 50 J/cm2, having a uniform intensity profile with variation in the optical laser beam diameter from the lower curve to the upper curve equal to 0.25, 0.5, 1, 2, 3, 3.5, 4, 5 mm, where the dermis is found between segments A and D and the sebaceous gland is found between segments B and C;

FIG. 4 schematically shows a laser system for the selective treatment of acne, according to the present invention;

DETAILED DESCRIPTION OF THE INVENTION

Figure 1:
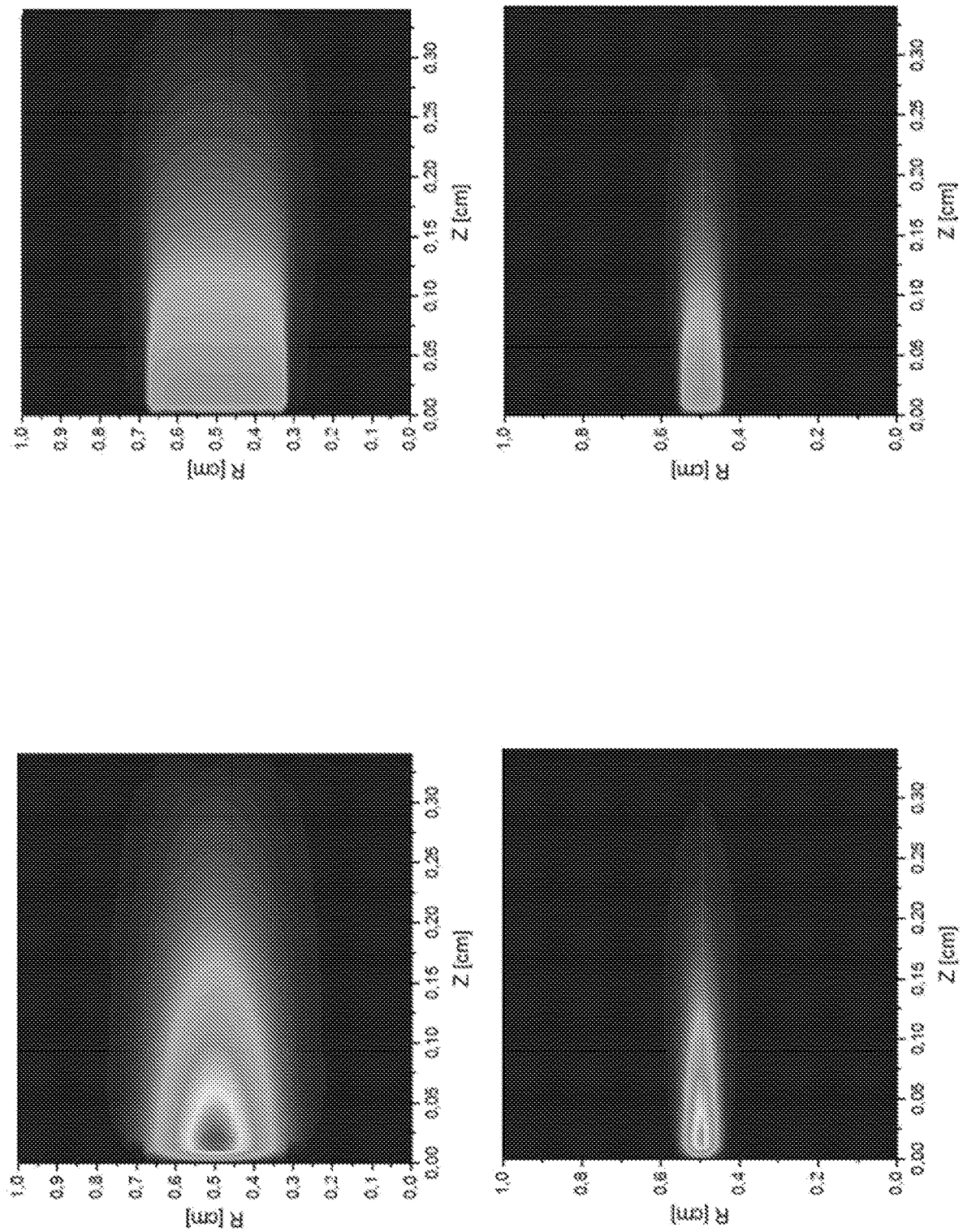

When the laser radiation, or more generally the light radiation, strikes a biological tissue, the first effect encountered is absorption of the photons by the tissue. Simultaneously photons scattering phenomena can be observed and in some cases phenomena of reflection which compete with the absorption. Physically these processes depend on the absorption coefficient of the tissues (μa), the scattering coefficient (μs) and the anisotropy coefficient (g) for the scattering, and on the ratios of the refraction indexes (n) for the reflection. Secondarily, the light absorbed by the biological tissue (below also defined target or target tissue), is converted into heat, energy, (ΔE) which can spread into the surrounding tissues. Consequently a temperature increase is recorded ((ΔT): ΔT=ΔE/(ρ×Cp) (equation 1) where ρ and Cp are the density and the specific heat of the tissue respectively). This temperature increase occurs not only on the target tissue but also in the neighbouring tissues. The time trend of the heat diffusion is governed by the thermal relaxation time (tr). The thermal relaxation time is defined as the time interval required in order that, given a Gaussian temperature distribution having a width equal to the diameter of the target tissue, its central value decreases by 50%. To a good approximation, tr [ms] is directly proportional to the square of the diameter of the target tissue and inversely proportional to the diffusion constant of the heat k: tr~(d^2)/(n×K) where n depends on the geometry of the target. For example, a sebaceous gland with length of 0.1 mm heats significantly in 0.5 sec. The energy absorbed by the target tissue and the fluence of the incident radiation are linked by means of the equation: ΔE≅μa×f×F (equation 2) where f represents the reduction fraction of the incident radiation intensity before reaching the target tissue. If the intensity, or better the fluence (F), defined as (Energy of the incident radiation)/(Area of the incident radiation spot), of the light radiation is sufficient, then the temperature increase destroys, for equation 2, the target tissue. It should be remembered that the fluence of the incident radiation (F) can be written in terms of laser power P and duration of the impulse t as: F=(Power×impulse duration)/(Spot area) and in this case we can talk about thermal damage and it is said that the light radiation has completed a treatment. Combining equation 1 and equation 2 we have:

$$\Delta T=(Tf-Ti)\cong[(P\times\tau)\times(f\times\mu a)]/[(\rho\times Cp)\times(\pi\times(\phi/2)2)] \quad \text{(equation 3)}$$

from which it is deduced that the temperature increase that induces the thermal damage is proportional:

a) to the absorption coefficient μa, and therefore depends on the wavelength of the incident radiation λ;

b) to the fraction f which decreases as the phenomenon of scattering increases and therefore as for the preceding point depends on the wavelength of the incident radiation and is correlated with the depth z to which the light radiation penetrates in the biological tissue;

c) to the energy of the incident radiation E and therefore to the power P of the radiating system by means of the relation E=P×τ;

d) to the irradiation time of the light radiation τ which if greater than the thermal relaxation time tr can induce a greater propagation of the heat beyond the target tissue and therefore an excessive temperature increase;

e) to the diameter φ and to the intensity distribution of the laser beam area;

f) to the initial temperature value Ti of the target tissue.

At this point it is appropriate to reflect on the biological significance of the temperature ranges (ΔT). In many human tissues, a temperature increase which induces a temperature in the range 50° C.-60° C. is sufficient to induce thermal damage but for higher values, highly undesired effects occur. In detail, in the temperature range 60° C.-70° C., the proteic structures and the collagen are denatured, while in the temperature range 70° C.-80° C., the nucleic acids disaggregate and the membranes become permeable. When the temperature reaches 100° C., vaporization of the water contained in the tissues occurs. It is concluded that the method of inducing thermal damage due to temperature increase (ΔT) in a target tissue by means of light radiation is of considerable interest for aesthetic and medical applications but, in said process, undesired temperature increases in the surrounding tissues, which can induce side effects like those described above, must be avoided. It follows that it is fundamental in the above-mentioned applications to control, during the process, all the physical parameters on which the temperature increase depends (equation 3). Of all the known studies, undoubtedly the publications by Prof R. R. Anderson are the most exhaustive. Selective photothermolysis (Anderson and Parrish, Selective photothermolysis: precise microsurgery by selective absorption of pulsed radiation in Science 220:524-527 1983) is based on the principle that an appropriate and maximum temperature increase (ΔT) occurs only in the selected target tissue, i.e. the damage induced by the light radiation or laser radiation is confined (Alora and Anderson, Recent Developments in Cutaneous Lasers in Lasers in Surgery and Medicine 26:108-118 2000). The technique of selective photothermolysis has been applied in different areas, including the selective treatment of acne. U.S. Pat. No. 6,605,080 illustrates a method and apparatus for the selective targeting of lipid-rich tissues, and teaches excellently the fluence values for the selective treatment of acne but leaves open the problem of penetration of the incident radiation into the biological tissue, assuming the same wavelength, considering that, again as stated in U.S. Pat. No. 6,605,080, the sebaceous glands are located at a depth, which is extensive, ranging from 1 mm to 4 mm from the surface of the skin. In this regard, the Applicant has noted that the penetration z of the radiation into the skin depends on the fluence and in particular the area, i.e. the diameter φ of the laser spot (FIG. 1). U.S. Pat. No. 6,605,080 indicates energy fluence ranges and time value ranges within which to perform the treatment of acne. Said value ranges do not consider the correlation, indicated mathematically in equation 3, existing with the penetration efficiency into the biological tissue. Again in U.S. Pat. No. 6,605,080 numerous wavelength ranges λ are suggested (880 nm-935 nm, 1150 nm-1230 nm, 1690 nm-1750 nm and 2280 nm-2350 nm) in which it is possible to selectively treat acne. As selective photothermolysis establishes, the best condition for the selective treatment of acne is when the absorption coefficient of the lipids ($\mu_{alip}$), in which the sebaceous gland is rich, is greater than the absorption coefficient of the water ($\mu_{aH20}$) in which the epidermis and dermis are rich, which is the tissue surrounding said gland. In this way a strong (selective) absorption of the sebaceous gland is obtained, and not of the surrounding tissues rich in water. Said condition occurs in all the wavelength ranges reported in U.S. Pat. No. 6,605,080 but the above-mentioned wavelength ranges are not equivalent for the purpose of the treatment of acne on human skin for two reasons:

1—passing from the range 880 nm-935 nm to the range 1690 nm-1750 nm the radiation contribution, in power P, which reaches the surface of the human skin is 10 times lower;

2—the effect of the scattering decreases as the wavelength increases and therefore the fraction f varies;

3—on the other hand, the penetration capacity of the light radiation increases with the wavelength.

Consequently, it is expedient to define one single wavelength range, or better a wavelength at which to emit the light source or better the laser source and optimize all the parameters for the selective treatment of acne for this wavelength. In 2006 Prof. Rox R. Anderson (Anderson et al., Selective Photothermolysis of Lipid-Rich Tissues: A Free Electron Laser Study Lasers in Surgery and Medicine 38:913-919 2006) carried out preliminary tests with a Free Electron Laser having wavelength at 1720 nm, reaching the conclusion that the selective lipid absorption band at 1720 nm could be of interest for the selective treatment of surface targets (i.e. maximum 2 mm skin depth) like the surface sebaceous glands. More recently, in 2011, an optical fibre source was developed based on Raman scattering able to emit laser radiation at a wavelength of 1708 nm (Alexander et al., Photothermolysis of sebaceous glands in human skin ex vivo with a 1,708 micron Raman fiber laser and contact cooling in Lasers in Surgery and Medicine 43:470-480 2011). The decision to use an optical fibre source based on Raman scattering, which therefore guarantees operation in the best wavelength range for the selective treatment of acne, means that the emerging beam has an intensity distribution with Gaussian profile. The limit of this solution is the use of said laser beam having intensity distribution with Gaussian profile. In fact, said beam is not the most suitable for the selective treatment of acne. As indicated by the authors, this profile can cause damage to the tissues located beyond the gland. In WO2011/084863A2 the same suggest using a laser beam having a more uniform spatial distribution, than the one typical of a laser beam with Gaussian profile, but without giving any practical indication of how to obtain it and how to make it effective for the selective treatment of acne. To reduce the damage induced by an excessive temperature increase of the skin surface, a cooling system has been introduced in the existing devices for the treatment of acne. There are numerous solutions that define a cooling system of the skin surface, i.e. they define an appropriate initial temperature value Ti. Many of these solutions are based on the emission of cryogenic liquids on the skin surface (Paithankar et al., Acne treatment with a 1,450 wavelength laser and cryogen spray cooling, Lasers in Surgery and Medicine 31:106-114 2002). These solutions are very often complex and not optimal when, during the treatment, the fluence value of the radiation that induces the temperature increase $\Delta T$ has to be drastically modified.

In conclusion, the known art has different approaches to the selective treatment of acne, but there is no one overall solution that allows control and dynamic modification of all the parameters that influence the temperature increase and which are mathematically discussed in equation 3. Consequently none of the solutions presented excludes the possibility of inducing biological damage to the tissues surrounding the sebaceous gland.

Figure 2:
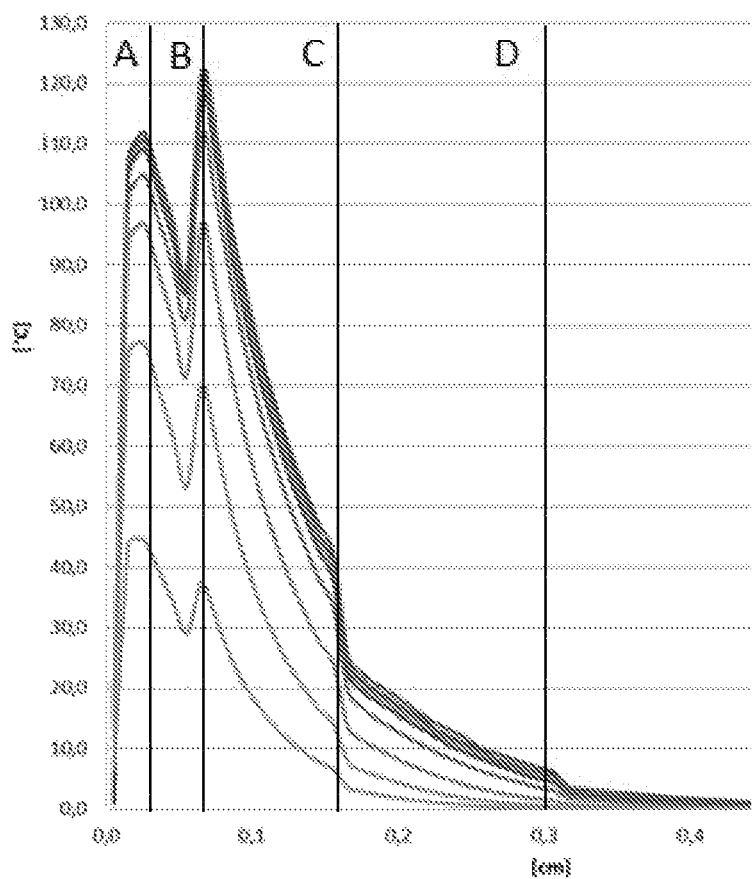
Figure 3:
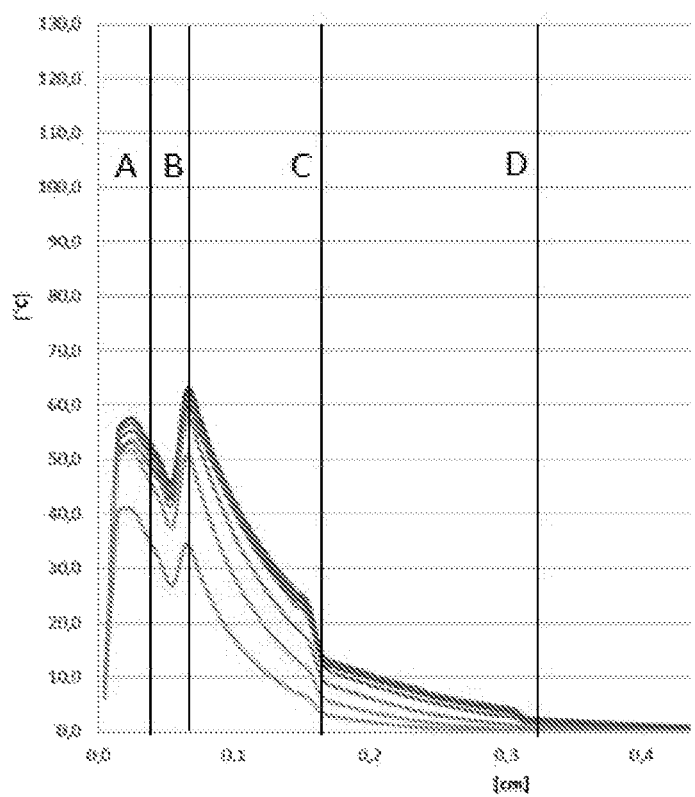
Figure 4:
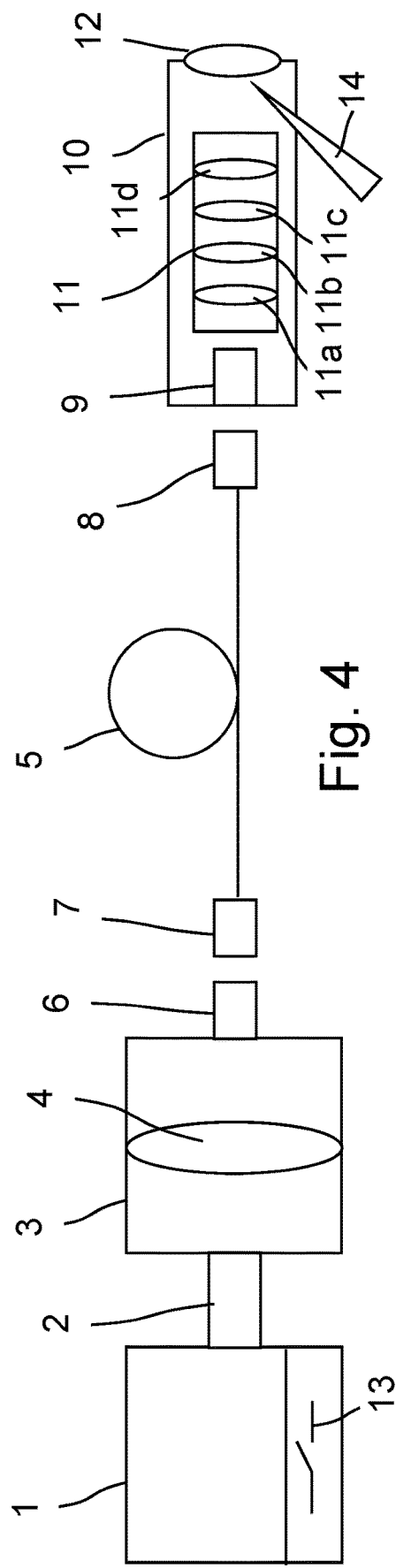

Monte Carlo simulations have been used to identify possible solutions for overcoming the limits of the known art described above. In these simulations, the target tissue is represented by a sebaceous gland located within the skin, in particular in the dermis. The gland is located, for example, at 0.6 mm from the skin surface and has a length of 1.0 mm. FIG. 1 illustrates the Monte Carlo simulations which on the left show the temperature increase ($\Delta T$) induced by a beam having a Gaussian intensity profile as the diameter of the laser radiation spot decreases, and on the right show the temperature increase ($\Delta T$) induced by a laser beam having a uniform intensity profile (also called "flat top") as the diameter of the laser radiation spot decreases. In this discussion, it is established that the laser beam intensity distribution is flat top, i.e. uniform, when the ratio ($\eta$) between the standard deviation of the intensity ($\delta I$) with respect to the mean value of the same intensity ($<I>$) is lower than a predefined value, here established at 15%. With the same fluence, it is observed that a beam having a uniform intensity distribution (flat top) induces a uniform temperature increase ($\Delta T$) in the first layers of tissue, i.e. those preceding the sebaceous gland. On the other hand, a laser beam having a Gaussian intensity profile induces a strong temperature increase ($\Delta T$) gradient, especially in the first layers of the tissue. This is particularly evident in FIG. 2. FIG. 2 shows the temperature increase ($\Delta T$) profile along the vertical axis of the sebaceous gland (R=0) induced by a laser beam having a Gaussian intensity profile (top left) and induced by a laser beam having a uniform intensity profile (bottom right) as the diameter of the laser beam varies. With a laser beam having a Gaussian intensity profile with diameter >1 mm a temperature increase >70° C. is induced in the layers of skin preceding the gland. Said increase is undesired for said layer of skin. Said effect does not occur with a laser beam having the same fluence as the preceding one but characterized by a uniform intensity distribution. Furthermore, with a laser beam having a uniform intensity distribution (flat top), as the diameter of the beam varies, the variance of temperature increase ($\Delta T$) is greatly reduced. It is concluded that a laser beam having a uniform intensity distribution is preferable with respect to a laser beam having a Gaussian profile intensity distribution for the purpose of the selective treatment of acne without the side effect of damage to the surrounding tissues. The analyses of the Monte Carlo simulations highlight that as the diameter of the incident laser radiation beam increases, the degree of penetration z of the radiation into the biological tissue increases. The advantage of modulating the diameter of the spot $\phi$ is therefore evident, maintaining the process fluence constant, in order to reach more or less deep skin layers. The use of a "flat top" beam is preferred in various applications (EP2407807, U.S. Pat. No. 5,658,275) and there are numerous techniques for obtaining such a beam profile starting from an intensity distribution of a multi-mode source. In particular in U.S. Pat. No. 6,532,244 a "flat top" beam is obtained by injecting a multi-mode laser beam (V-number >2.405) into two multi-mode fibres, the first having a Vnumber lower than the second; on the second fibre, called remote control fibre, the fibre is bent with an appropriate radius of curvature (known as bending technique). Solutions are also known (WO2011070306) in which a laser beam having a Guassian intensity profile is converted by means of non-linear materials into a beam having an intensity distribution. A laser beam having an arbitrary intensity profile can be made flat top also by means of special diffractive optics. Said solutions are not particularly optimal. In detail, the application in which a radius of curvature is introduced on a fibre, in order to obtain a beam with a uniform intensity distribution, is not advisable due to problems of power loss induced by the curvature (D. Marcuse, "Curvature loss formula for optical fibers", J. Opt. Soc. Am. 66 (3), 216 (1976)) and the probability of creating micro fractures in the fibres subject to curvature. The decision to switch from a fibre with a V-number V1 to a fibre having a V-number V2, such that V2>V1, requires the use of optics which have the effect of shattering the wave front and inducing losses in the light intensity. Lastly, solutions that entail the use of discrete optics, such as microlenses, or non-linear materials induce considerable power losses in the passage of the laser radiation through the non-linear materials. Lastly, it is also known that to obtain a beam having a uniform intensity distribution the initiation of the non-uniform beam in the fibre must occur with appropriate angles (Shealy and Hoffnagle Laser beam shaping profiles and propagation in Appl. Optics Vol 45 2006).

A laser device for the selective treatment of acne, according to the present invention, comprises a laser source 1 in optical fibre based on the Raman effect. The source 1 terminates in an optical collimator 2. The collimator 2 is optically aligned with an optical fibre 5 by means of an opto-mechanical interface 3. The opto-mechanical interface 3 is composed of a linear and angular micrometric adjustment system (x-y-z, θ-φ) which by means of a lens 4, positioned inside it, focuses the collimated beam emerging from the collimator 2 inside the core of the fibre 5. The opto-mechanical interface 3 terminates in an SMA connector 6 and the multi-mode fibre 5 begins with an SMA connector 7.

The fibre 5 terminates in an SMA connector 8, which is connected to a handpiece 10, which is placed in contact with the biological tissue during the treatment by means of an SMA connector 9 cooperating with the SMA connector 8.

The handpiece 10 comprises an optical zoom system 11 which allows the laser beam emerging from the fibre 5 to be magnified.

The handpiece 10 comprises at its end a sapphire window 12.

The laser source 1 comprises a switch 13 which interrupts transmission of the laser beam and allows adjustment of the duration of the laser impulses sent.

By appropriately activating the switch 13 it is possible to send laser impulses of the desired duration and separated by desired wait times.

The source 1 emits at the wavelength of 1726 nm or more generally in the wavelength range 1720 nm-1730 nm. Not only in said range is the absorption coefficient of the lipids greater than the absorption coefficient of the water, $\mu_{alip}=10$ cm−1>μaH2O=6 cm−1 (@1720 nm), but the scattering coefficient (3.5 cm−1 @1720 nm) is greatly reduced with respect to the absorption coefficient of the lipids (10 cm−1 @1720 nm) guaranteeing the condition that almost all the incident photons are absorbed by the biological tissue. The radiation emerging from the optical collimator 2 is collimated and has a diameter in the range 3 mm-5 mm. The source 1 can emit light radiation in continuous mode or in pulsed mode. The laser source 1 is provided with a power regulator and a switch which provides the pulsed emission of the source. Given the nature of the source 1, the intensity profile of the radiation emerging from the collimator 2 has a Gaussian form. In an alternative configuration, the laser source can be terminated with a fibre having a V-number>2.405.

The opto-mechanical interface 3 is composed of a linear and angular micrometric adjustment system (x-y-z, θ-φ) which by means of a lens 4 focuses the collimated beam emerging from the collimator 2 inside the core of the fibre 5.

The fibre 5 has the following characteristics:

1. the diameter φ and the numerical aperture NA of its core, are not functional to the creation of a beam having a uniform intensity distribution but are functional to ensuring that the injection of the collimated laser radiation by means of the lens 4 is maximized so as not to induce losses in light intensity and undesired overheating of the SMA connector 7;
2. V-number>2,405;
3. the core can have a circular, square or rectangular profile;
4. a length L so as to obtain after a certain value of L, called L*, a laser beam having a uniform intensity distribution;
5. it is wound with a radius of curvature which is functional only to housing in the device and is not such as to induce radiation intensity losses due to the bending.

Figure 5:
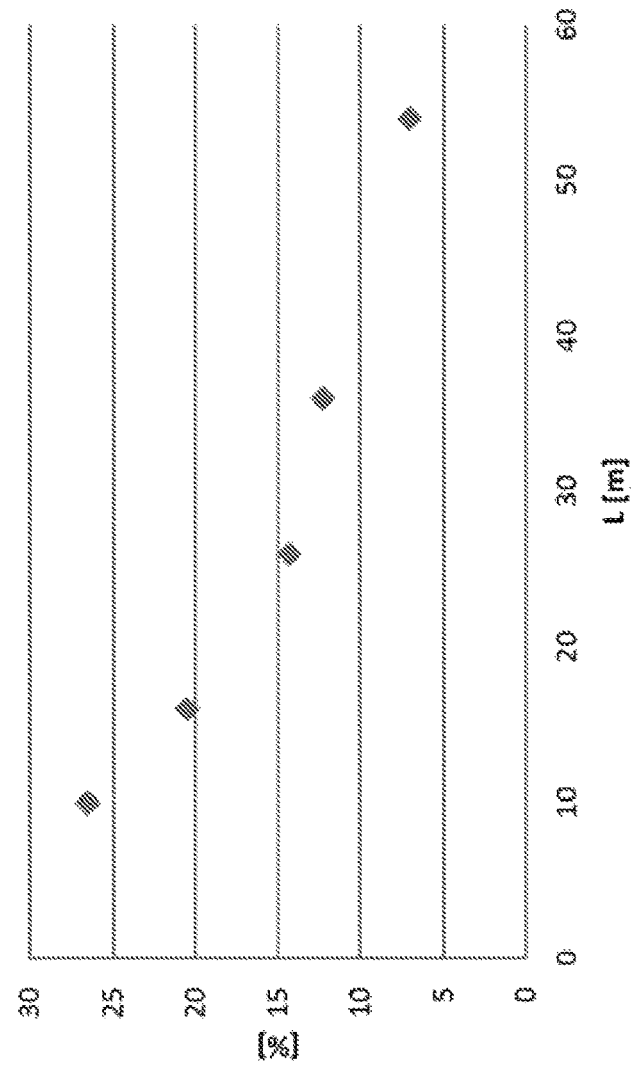
FIG. 5 shows the evolution of the laser beam intensity distribution at 1726 nm with variation in the length of the fibre L for a fibre having a core diameter of 200 micron and core numerical aperture 0.22.

FIG. 5 shows the intensity distribution of the laser beam emerging from the fibre 5 for different values of the fibre length L. By way of example, for a fibre having V-number=78.50, the value of L for which the intensity distribution is uniform η≤15% is L* is equal to or greater than 25 m. If we consider η≤20%, the length L* is equal to or greater than 15 m.

It should be noted that when the length of the fibre L is L≥L*, the parameter η is independent of the release conditions, for example the specifications of the lens 4. Therefore, the achievement of this latter result makes one of the physical parameters η functional to the selective treatment of acne independent of any optical alignment conditions of the system which could change over time. Furthermore, the technical choice of using only the length parameter of the fibre as a control element for producing the flat top beam has the advantage of not introducing any type of power loss P of the laser source 1. In conclusion: the technological solution chosen to obtain the appropriate uniformity of the intensity distribution η≤15% for the selective treatment of acne is independent of the power P of the laser radiation necessary for the treatment.

It has been ascertained that L* depends on the V-number value of the fibre and the wavelength of the incident laser radiation. In particular it has been ascertained that L* decreases as the V-number increases and L* increases as the wavelength decreases. In conclusion not only the wavelength range 1720 nm-1730 nm selected is advantageous for the values of the coefficients described above but the intensity distribution uniformity value obtained is lower. In the solution proposed, the radius of curvature with which the fibre is housed in the device does not have any effect of rendering the intensity distribution uniform. In conclusion the fibre 5 which meets the 5 above-mentioned conditions is the element that transforms the laser beam having an intensity distribution with a Gaussian intensity profile emerging from the collimator 2 into a laser beam having a uniform intensity distribution. In a similar manner, the fibre 5 can transform a non single-mode laser beam with a non-uniform intensity distribution into a beam having a uniform intensity distribution.

The fact that the fibre 5 and the handpiece 10 are connected by means of two SMA connectors makes the handpiece 10 a replaceable element, i.e. it is extremely useful in the application field in the event of failure or damage thereof during the treatment.

The zoom system 11 consists of an optical system adapted to produce on the sapphire window 12, which is positioned in the image plane of said system, a magnified image of the output surface of the fibre 5 guaranteeing the same intensity distribution.

The optical zoom 11 is an optical system composed of 3 lenses. By way of example a first lens 11*a* is a flat convex lens which focuses the beam emerging from the fibre 5 on the second lens 11*b*. The second lens 11*b* is a bi-concave lens. The third lens 11*c* is a bi-convex lens which transforms the magnified beam coming from the second lens 11*b* into a collimated beam which reaches the window 12. The second bi-convex lens 11*b* moving between the first 11*a* and the third lens 11*c* disperses the light rays, modifying the magnification of the beam emerging from the fibre 5.

The movement of the second lens 11*b* occurs in a known manner and can be adjusted from the outside in continuous mode.

In an alternative solution after the third lens 11*c* it is possible to introduce a further fourth pianoconvex lens 11*d* which allows the magnified beam to be focused inside the biological tissue. The degree of magnification "m" achieved by the zoom system 11 is variable thus obtaining, dynamically during the treatment, the most appropriate diameter ϕ of the laser beam. This optical configuration does not vary the intensity distribution of the laser beam.

Figure 6:
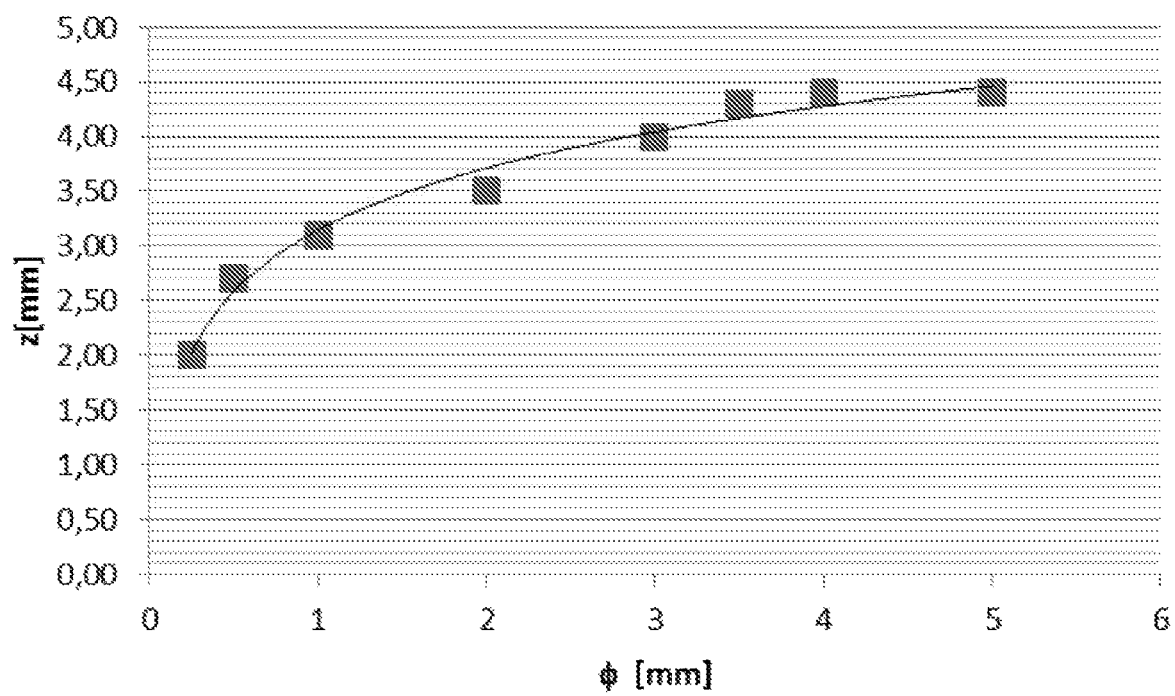
FIG. 6 shows the dependence of the penetration of the radiation into the biological tissue z as a function of the diameter of the laser beam $\phi$.
Figure 7:
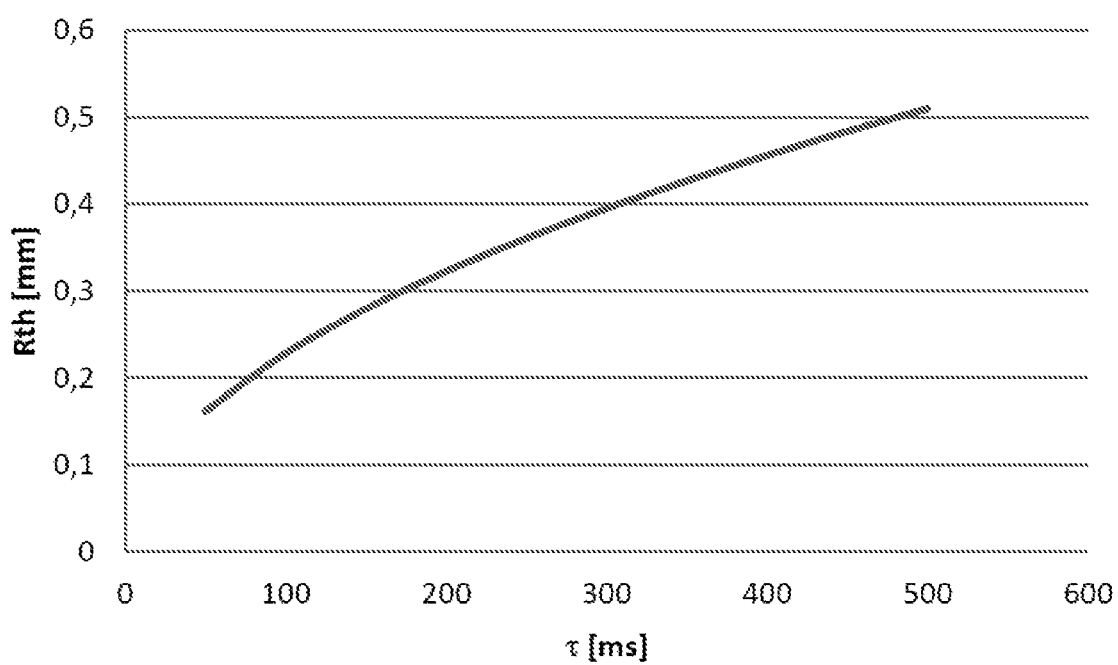
FIG. 7 shows the dependence of the thermal path $R_{th}$ versus the time duration of the impulse $\tau$.

By way of example, hypothesizing that the fibre 5 is a fibre having a core diameter of 0.2 mm, the zoom system 11 allows a magnification ranging from 2.5× to 25× to be obtained dynamically, so that it produces in the sapphire window a laser beam diameter varying in the range 0.5 mm-5.0 mm, and more preferably 1.5 to 3.5 mm. This solution has the unique characteristic of modifying, during the treatment, two process parameters: the fluence, and therefore the temperature increase ΔT in the target tissue and the dimension of the emerging laser beam, and therefore the depth level in the tissue reached by the radiation (FIGS. 6 and 7). It is underlined that said dynamism does not affect the uniformity level of the laser beam intensity distribution. It is furthermore possible to introduce a feedback system which connects the magnification produced by the system 11, and therefore the diameter of the spot ϕ, with the adjustment of the power P emitted by the laser source 1 so that for each diameter of the spot that reaches the surface of the skin, the appropriate fluence is obtained. By way of example, if we wanted to apply 50 J/cm2 with a beam having uniform intensity distribution and diameter 3.5 mm, a laser power of approximately 60 W would be required. If during the same treatment it were necessary to reduce the fluence, for example from 50 J/cm2 to 30 J/cm2, without varying the process depth, i.e. maintain the spot at 3.5 mm, it is sufficient to reduce the power of the source 1 to approximately 36 W. A further example: if we wished to apply 30 J/cm2 with a beam having uniform intensity distribution and diameter 4.0 mm, a laser power of approximately 62 W would be required. If during the same treatment it were necessary to reduce the process depth without varying the fluence, then it would be sufficient to reduce the dimension of the spot to 2.0 mm and the power of the laser source 2 to 19 W. FIG. 6 shows the dependence of the process depth z on the dimension of the beam ϕ. Note that during the treatment of acne, it is not problematic to reach the sebaceous glands arranged in the more superficial skin layers, but it is more difficult to reach the glands located at a depth. The proposed solution allows this criticality to be solved as it permits equal treatment of the surface glands and the deeper glands or more generally ranging from 0.5 mm to 5.0 mm, in a dynamic manner. A further advantage of the proposed solution is evident if we consider the positions of the pain receptors n the skin. They are located in the surface areas of the skin z<2.5 mm and have a mean density of approximately 100/cm2. It follows that to treat the sebaceous glands located near the surface of the skin, for example in the range z∈[0.5 mm; 2.5 mm], and reduce the stimulation of the greatest number of receptors, it is expedient to work with beams having diameters ϕ<2.0 mm.

In some cases to reduce the damage to the surface layers of the skin, it is expedient to reduce the temperature of said layers. To reduce the temperature of the first layers of skin, a cooling system can be used (not shown), connected to the handpiece 10, which by means of an air flow emitted from a tube 14 can lower the temperature of the sapphire window 12 positioned after the zoom system 11; the sapphire window 12 is placed in contact with the biological tissue to be treated. Said cooling system allows the temperature to be adjusted in a range from −10° C. to +10° C. This solution offers a dual advantage: on the one hand water flows are not used to cool the window 12 and on the other, the air flow that strikes the inner side of the window 12, i.e. the one opposite the contact surface with the biological tissue to be treated, prevents the formation of condensate produced by the low temperatures to which the element 12 is exposed. The sapphire window 12 is more generally an optical window chosen for its high thermal conductivity value and transparency to the radiation of interest but does not alter the form of the laser beam intensity profile.

Figure 8:
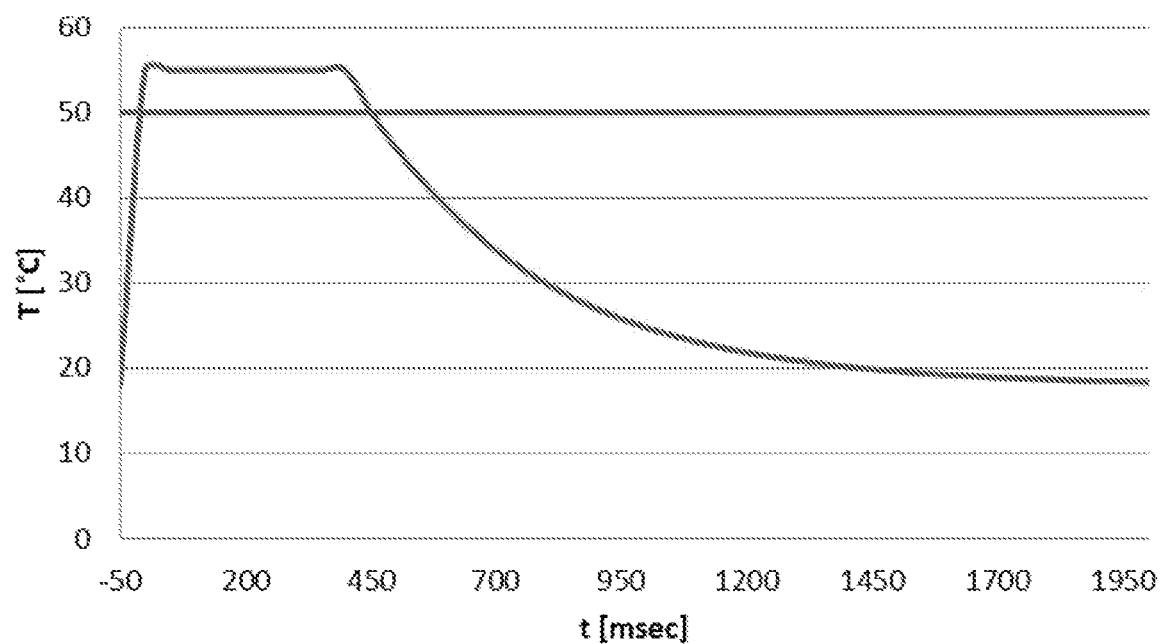
FIG. 8 shows the temperature variation of the sebaceous gland with one single impulse having a duration of 400 ms.
Figure 9:
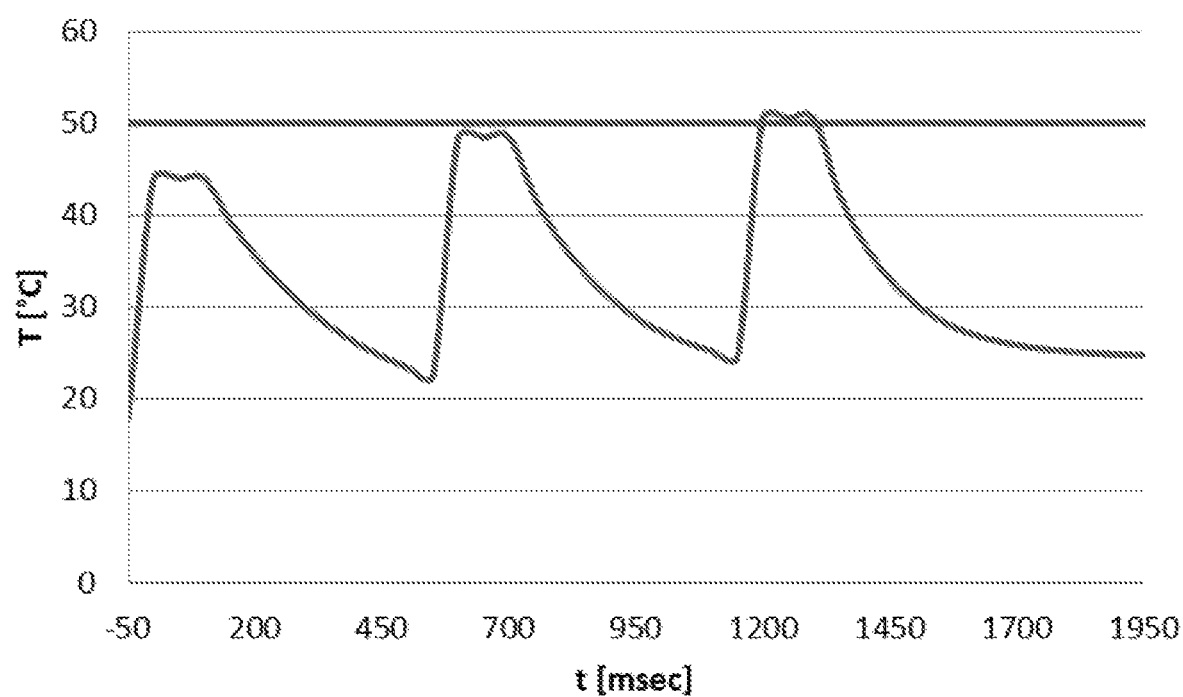
FIG. 9 shows the temperature variation of the sebaceous gland with a sequence of three impulses with duration of 100 ms.

The cooling process of the various layers of the skin below the skin surface is regulated by the laws of thermodynamics. Taking account of this and the presence of the switch 13 of the laser source 1, the duration of the impulse or the series of impulses to be applied can be regulated, as shown in FIGS. 8 and 9.

At the instant t=0 msec the sebaceous gland is irradiated with a power P for a time τ. The temperature of the gland passes from the basal temperature of the tissue $T_{base}$ to the maximum temperature $T_{peak}$, i.e. a temperature increase ΔT is obtained. The duration of the laser impulse τ is lower than the thermal relaxation time of the target tissue (in the example it is 450 ms), which as previously discussed depends on the geometry of the target, so as not to induce heating of the tissue surrounding it. Following the radiation, the temperature decreases and after a certain time the temperature of the gland returns to $T_{base}$.

If the time duration of the impulse τ, i.e. the length of time the power P is administered, is not sufficient to induce a temperature increase ΔT which produces thermal damage in the sebaceous gland, the time duration of the impulse τ is increased until the maximum limit is reached represented by the thermal relaxation time. This results in the tissue regions surrounding the gland heating due to release of the energy absorbed by the gland. The extent of these regions depends on the duration of the impulse, and the thermal path Rth (FIG. 7), which represents the radial propagation of the energy released by the irradiated sebaceous gland, depends on the time duration of the radiation.

The proposed solution allows heating of the portions of tissue surrounding the sebaceous gland to be avoided by means of a time modulation of the laser impulse. FIG. 9 shows an example of said modulation for a sebaceous gland with thermal denaturation value 50° C. and tr~500 ms. FIG. 8 shows the temperature value induced by a source which emits an impulse with duration of 400 ms. FIG. 9 shows the temperature value induced by the same source which emits three impulses with duration of 100 ms each, spaced by a time of 500 ms according to the present invention. In the first case the radial propagation is 0.45 mm, in the second case, the one according to the present invention, said value is reduced by 50%, i.e. it reaches the value of 0.22 mm. By way of example the impulse of the source 1 can be modulated in the range between 10 ms and 500 ms.

If single laser sources of appropriate power are not available to perform the selective treatment of acne, an alternative solution is introduced in which two or more sources are combined.

The invention claimed is:

1. A laser device for the selective treatment of acne comprising: a laser source (1) terminating in an optical collimator (2), which supplies a laser beam; said laser source (1) comprises a switch (13) which allows impulses of said laser beam of pre-defined duration to be transmitted; an opto-mechanical interface (3) comprising a lens (4) focusing the laser beam received from the optical collimator (2); an optical fibre (5) connected to said opto-mechanical interface (3); characterized in that said optical fibre (5) has a length greater than 15 m; and said device comprises a handpiece

(10) connected to said optical fibre (5) where said handpiece (10) comprises an optical zoom system (11) which allows the diameter of the laser beam emerging from said handpiece (10) to be varied from 0.5 mm to 5 mm.

2. A device according to claim 1 characterized in that said laser source (1) emits a laser beam at the wavelength of 1726 nm.

3. A device according to claim 1 characterized in that said laser source (1) is single-mode.

4. A device according to claim 1 characterized in that said optical fibre (5) is a multi-mode fibre.

5. A device according to claim 1 characterized in that said optical fibre (5) produces at its output a laser beam having a flat top beam intensity distribution, where the ratio between the standard deviation of the intensity with respect to the mean value of the same intensity is lower than 20%.

6. A device according to claim 1 characterized in that said handpiece (10) comprises at its output a sapphire window (12).

7. A device according to claim 6 further including a cooling system for sending air at a predefined temperature to the inner surface of said sapphire window (12).

8. A device according to claim 1 characterized in that said switch (13) is controlled so that the duration of an impulse is in the range between 10 ms and 550 ms.

* * * * *